US007945450B2

(12) United States Patent
Strawder

(10) Patent No.: US 7,945,450 B2
(45) Date of Patent: *May 17, 2011

(54) METHOD FOR MONITORING RADIOLOGY MACHINES, OPERATORS AND EXAMINATIONS

(76) Inventor: Glenn G. Strawder, Laurel, MD (US)

( * ) Notice: Subject to any disclaimer, the term of this patent is extended or adjusted under 35 U.S.C. 154(b) by 1344 days.

This patent is subject to a terminal disclaimer.

(21) Appl. No.: 09/865,696

(22) Filed: May 29, 2001

(65) Prior Publication Data
US 2002/0010395 A1    Jan. 24, 2002

Related U.S. Application Data

(60) Division of application No. 09/220,064, filed on Dec. 23, 1998, now Pat. No. 6,282,513, which is a continuation-in-part of application No. 08/720,036, filed on Sep. 27, 1996, now abandoned.

(60) Provisional application No. 60/004,891, filed on Oct. 6, 1995.

(51) Int. Cl.
*G01T 1/161* (2006.01)
*G01N 33/483* (2006.01)
*G06Q 50/00* (2006.01)

(52) U.S. Cl. ............... 705/2; 702/19; 250/363.02

(58) Field of Classification Search ............ 705/2, 3; 434/262
See application file for complete search history.

(56) References Cited

U.S. PATENT DOCUMENTS

| 3,916,192 A | 10/1975 | Schmitmann et al. |
| 3,932,759 A | 1/1976 | Brudin |
| 3,999,044 A | 12/1976 | Grim |
| 4,158,138 A | 6/1979 | Hellstrom ............... 378/116 |
| 4,160,906 A | 7/1979 | Daniels et al. |
| 4,491,725 A * | 1/1985 | Pritchard ............... 705/2 |
| 5,088,981 A * | 2/1992 | Howson et al. ............ 604/31 |
| 5,325,293 A * | 6/1994 | Dorne ................. 705/2 |
| 5,359,509 A * | 10/1994 | Little et al. ............ 705/2 |
| 5,417,213 A * | 5/1995 | Prince ................ 600/413 |
| 5,544,157 A * | 8/1996 | Wenstrup et al. .......... 378/18 |
| 5,585,841 A | 12/1996 | Hardin ................ 348/163 |

(Continued)

FOREIGN PATENT DOCUMENTS
GB    2113828 A    8/1983
(Continued)

OTHER PUBLICATIONS

Bautista, Cecilia L., "Meeting the challenge of cost containment: a case study using variance analysis." Fall, 1994, Topics in Health Care Financing, v21, n1, p13(11).*

(Continued)

*Primary Examiner* — Robert W Morgan
*Assistant Examiner* — Rachel L Porter

(57) ABSTRACT

The method of creating at least one standard protocol or pattern about the operator, the patient, the examination and/or the machine being used. Monitoring, creating and recording data about at least one of them during the actual performance of the examination. Next, compare this data to a standard protocol to produce certain results or findings about either the revenues and expenses surrounding the exam, the operators performance and skill levels during the exam, the productivity of the machine and operator, etc. Networking the data from more then one machine to a central computer and performing various analyzes, computations and/or calculations on the data from the various machines. The results will provide individual as well as combined totals for all of the machines in a department that download data to the computer.

18 Claims, 2 Drawing Sheets

U.S. PATENT DOCUMENTS

| | | | | |
|---|---|---|---|---|
| 5,737,386 A | * | 4/1998 | Strawder | 378/95 |
| 5,740,267 A | | 4/1998 | Echerer et al. | 382/132 |
| 5,797,849 A | | 8/1998 | Vesely et al. | 600/461 |
| 5,848,198 A | | 12/1998 | Penn | 382/276 |
| 6,006,191 A | | 12/1999 | DiRienzo | 705/2 |
| 6,119,033 A | | 9/2000 | Spigelman et al. | 600/426 |

FOREIGN PATENT DOCUMENTS

| | | | | |
|---|---|---|---|---|
| GB | 2113828 A | * | 8/1983 | |
| JP | 03139335 A | | 6/1991 | |
| JP | 03139335 A | * | 6/1991 | |
| JP | 07057119 A | | 3/1995 | |
| JP | 07057119 A | * | 3/1995 | |

OTHER PUBLICATIONS

"Product Brief", Information Technology Report, v5, n6, Dialog File 636, Access. No. 03857032. Apr. 1998.*

"Product Name: Front Office Practice Management System (016842)", Systec Computer Services, Dialog File 256 Access No. 01016842, Jul. 1987.*

"Smaller radiology systems: the next big thing?", HealthWeek, p25, Dialog File 16, Access No. 01853121, Sep. 1991.*

Johnsson, J., Imaging. (new cost perspectives of diagnostic imaging), Hospitals, v64, n21, p24(10) Dialog File 149, Access No. 01247919, Nov. 1990.*

Pickens et al., "Qualitative and quantitative evaluation of charge capture by a radiology information system", Journal of Dignal Imaging, p. 49-53, Dialog File 155, Access No. 06570191, Feb. 1990.*

"Symposium of the Imaging Science and T chnology Group of the Royal Photographic Society. Recent dev lopments in medical imaging.", Jurnal of Photgraphic Sci nce, vol. 37, No. 3-4, Dialog File 2, Access No. 03607767, 1989.*

Access # : 01247919/9 Imaging new cost . . . diagnostic imaging, Dialog File 149, Nov. 1990.

Access #: 01853121/9 Smaller radiology . . . : the next big thing?, Dialog File 16, Sep. 1991.

Access #: 01016842/9 Front office practice management system Dialog File 265, Jul. 1987.

Access #: 03857032/9 Information Technology Report, Dialog File 636, Apr. 1998.

Access #: 06570191 Qualitative and quantitative eval . . . system Dialog File 155, Feb. 1990.

Access #: 03607767 Symposium of Imaging Science . . . Society Dialog File 2, 1989.

See attached "Notice".

* cited by examiner

METHOD FOR MONITORING RADIOLOGY MACHINES, OPERATORS AND EXAMINATIONS

RELATED CASES

This is a divisional application of my application Ser. No. 09/220,064 filed Dec. 23, 1998, now U.S. Pat. No. 6,282,513 entitled A Quality Assurance Method for a Machine and an Operator which is a continuation-in-part application of my prior application Ser. No. 08/720,036 filed Sep. 27, 1996, now abandoned entitled Method For Measuring Patient Radiation Dose, which claims the benefit of my provisional application Ser. No. 60/004,891 filed Oct. 6, 1995, entitled Patient Dose Monitoring Method.

BACKGROUND OF THE INVENTION

The present invention relates to an apparatus and method capable of producing findings which monitor the productivity of an x-ray machine and its operator. The skill and performance of the operator of the x-ray machine during an examination or procedure, is also monitored.

The Radiology department of a hospital may have many machines such as X-ray machines, C.T. scanners, MRI scanners, etc. Also, a Radiology department is similar to a fee for service type of business. That is, when the department provides some type of service such as taking an x-ray picture of a particular body part, and then charge a fee for that service. A Radiology department may perform many different types of examinations, many times daily. These exams generate large sums of expenses as well as revenue. Keeping track of the who, what and why's about an expense and revenue could be helpful in making good business decisions.

Basically, a patient is charged a fee for every x-ray picture (radiograph) taken. The fee normally has several different items of cost involved in its total. Each exposure of an x-ray picture reduces the life of the x-ray tube and possibly some other parts of the machine, hence a fee is charged to cover this expense. Also, every time an x-ray exposure is delivered to a patient the X-ray Technologist (operator) performs several different tasks. The basic task or steps performed by the operator for each exposure delivered are: 1) the operator takes time and formulate how much radiation will produce a good x-ray image of the body part under investigation, 2) the operator sets the parameter control dials of the machine to the right levels for the exposure, 3) at some point in time prior to the actual deliverance of the exposure, the operator must physically position the body part to the correct position, 4) the operator places or replaces an x-ray film in proper alignment with the exposure, and 5) the operator must finally press the exposure or release button to deliver the exposure. These basic steps are an operator's standard duties and are considered an expense and part of the total fee charged to the patient for the service of producing an x-ray picture. Other expenses considered in the total charge of the fee may include such items or services as: the cost of the x-ray film, the cost to develop the film, the cost to interpret the x-ray film by a doctor, etc. Also, there is generally some sort of profit included. The above basic efforts of an operator are repeated many times a day in an active x-ray department (room). Having a record of the process that surrounds the production of each x-ray picture during an examination can be very useful when trying to determine such things as: total revenues and expenses for the examination, operator skill and performance levels for the examination, operator and machine daily productivity and much more.

SUMMARY OF THE INVENTION

The word "examination" refers to all steps and procedures for taking the desired number of x-rays or pictures of a part of a human body, animal or other object.

An X-ray machine, C.T. scanner and/or MRI scanner of an institution, for example, may be called upon to make pictures of hundreds of body parts. For each one of these numerous body parts this invention contemplates that at least one standard protocol be developed and stored in the memory of a computer used with the machine. At least one standard protocol program for each particular type of examination or body part may be provided in the form of software sold to the hospital by a supplier, or composed by the hospital.

The invention is basically a method of creating at least one standard protocol or pattern about an operator, a patient, an examination and/or the machine being used, then monitoring at least one of them during the actual performance of the exam. The inventions creates and records certain data about at least one of them. Then compares this data to a standard protocol to produce certain results or findings about either the revenues and expenses surrounding the exam, the operators performance and skill levels during the exam, the productivity of the machine and operator, etc. A mainframe and/or central computer performs various analyzes and calculations on the data from one or more of the imaging machines the invention is connected to in a Radiology department. These results will provide individual and combined totals for all of the machines that download data to the mainframe.

In general, a standard protocol program describes a particular type of pattern, sequence, cost, etc. that describes how to take a picture of a body part or perform an examination. That is to say, a standard protocol may outline the normal sequence in taking the desired number of x-rays of a body part. A standard protocol may outline the normal time frame for each position to be performed by the operator during the examination. A standard protocol may also list the cost (revenues and expenses) of each item used by an operator to perform an examination. A standard protocol may outline the routine number of exams performed on a machine per shift, per day, etc. A standard protocol may also include typical settings of the input parameters of the machine for each such view. The above input parameters of the machine, for a given view would include for example, the voltage, the current (MA) and the duration of the exposure.

In addition to technical data described above a standard protocol may include pricing data, such as the cost (to the patient) of the x-ray films of different sizes, the cost (to the hospital) of the x-ray films of different sizes, the hourly rate of the technologist to be charged to the patient (dollars per hour or per examination), the hourly rate of the technologist to be charged to the hospital (dollars per hour), etc.

There are many different types of standard protocol programs that can be created surrounding the machine, the operator, the patient and/or a particular type of examination being performed. Each standard protocol is designed to produce data that is different than the data produced by a different type of standard protocol that is created about the machine, the operator, the patient and/or the examination being performed. Therefore, each standard protocol is designed to produce a slightly different result or finding about the machine, the operator, the patient and/or the examination being performed. That's because each standard protocol may be made up of data that is slightly different.

When the technologist takes the actual x-rays of any given body part of an actual patient, he or she enters in the computer all data on the actual x-rays taken (except for standard costs such as the cost of film, hourly rates, cost of contrast agents, cost of medications, cost of materials, time duration of exam, etc.).

The computer will compare the data entered relating to the actual x-rays taken, with a standard protocol. This comparison may produce results or findings relating to the machine, the operator, the patient and/or the examination being performed. This comparison may show that nothing happened different that what is found in a standard protocol. This comparison may show that the operator performed their task worst then or better than a standard protocol. This comparison may show that the examination was performed exactly as set forth in a standard protocol. This comparison may show that the operator made a mistake and may need re-training to strengthen a particular skill or performance area. This comparison may show how productive a particular machine is. This comparison may fix the blame for any costs set forth in the actual x-ray data that are not found in the standard protocol. This comparison may show the total cost to be charged to the patient as well as any expenses that the institutions must also absorb for an examination.

In the preferred form of the invention, the x-ray technologist operates the keyboard of a computer and the computer automatically sets the input controls of the x-ray machine or other imaging machines. It is, however, within the broadest aspects of the invention, for the computer to be free of connections to the x-ray machine, in which case the input data is separately entered into the x-ray machine and the computer. When the technologist takes the actual x-rays or pictures of any given body part of an actual patient, he or she enters in the computer data surrounding the examination and the use of any given machine.

If the hospital has a number of X-ray machines, C.T. scanners and/or MRI scanners, all of the computers for the various machines may be in a network that also includes the computer of the supervisor or manager. The supervisor's computer may develop any available information, pricing data etc. that is stored in any computer in the network individually or in combination. Such information includes the hourly rate of the technologist to be charged to the patient (dollars per hour), the fee for a time duration for taking each view, the cost (to the patient) of additional x-ray films of different sizes, the cost (to the patient) of contrast agents, the cost (to the patient) of medications, the cost (to the patient) of materials used, etc.

The invention may employ a second computer. This second computer compute totals for all machines, as for example it may show the combined total charges for the day, the combined total number of examinations for the day, the combined total of each type of examination for the day, the percentage of the daily workload a particular operator does for the day, the percentage of the daily workload a particular machine or room does for the day, etc. This second computer may compute and produce results or findings related to the machine, the operator, the patient and/or the examination individually or in combination.

DETAILED DESCRIPTION OF THE INVENTION

I will describe my invention as it may applied to taking X-rays of the Lumbar spine series, but with the understanding that this description is simply an example since the taking of X-rays of any other part of the human body would involve substantially the same apparatus and a procedure must to be performed.

Figure 1:
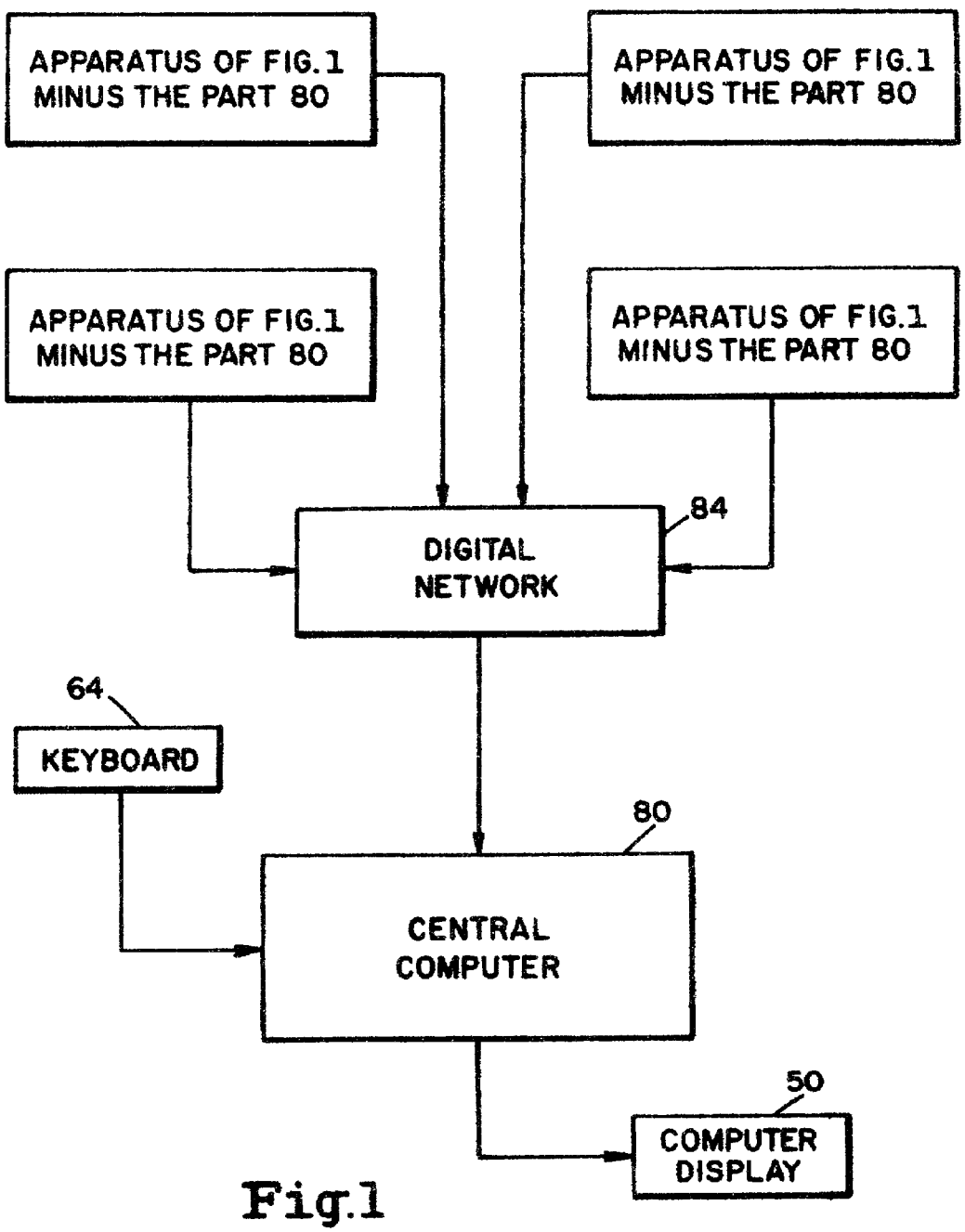
FIG. 1 is a block diagram of the present invention.

The preferred form of the invention enables an x-ray technologist to use x-rays as part of the examination of a patient. FIG. 1 shows a basic form of the present invention with an x-ray machine or tube 10, a collimator 20 and a computer 60 and mainframe 80. The following is a description of a manager operating a computer 60 unit and central computer 80 and creating a standard protocol program that is capable of producing data that will help evaluate the skill levels of an operator during the actual performance of a particular type of x-ray examination. This example includes a sample of the type of data that is needed to create this particular type of standard protocol as well as the step method that a manager may take when creating this particular type of protocol. First, a manager turns computer 60 on by depressing an "on" button switch. Next, the manager may view on the display screen 50 a menu which lists various available options. One option would be to call up a standard protocol programmed by the manufacturer used to produced data that helps evaluate the skill levels of an operator during the actual performance of a particular examination and another option would be for the hospital to create its own standard protocol program about the same examination. In light of that, the manager may input data via keyboard 64 or by touching a soft key (not illustrated) located on display screen 50. He or she selects the option labeled "create a standard protocol" from the list. The manager then enters in computer 60 the name of the type of examination or body part 90 that this particular standard protocol is going to be created or built for. The type of body part 90 I will use in this example is of the lower back region of a person called, "a Lumbar spine examination or series". In general, the abdominal cavity is generally more circular than oval in shape (if you take a cross-section of the cavity) in most people. The lumbar spine vertebrae are one of many different body parts that are located in the abdominal cavity. The lumbar spine vertebrae are not located in the center of the abdominal cavity. The lumbar vertebrae are located in the center portion of the back wall area of this cavity. And when a person is lying down flat on his back, the posterior aspect of a lumbar spine vertebrae (called, "the spinous process") is probably touching or pressing up against the surface that the person is resting on.

When rotating the abdominal cavity to demonstrate each of the positions required in the series, the thickness of the body part will change considerably as the body is turned or rotated. The amount of radiation (or strength of the x-ray beam needs) will differ for at least four (4) of the five (5) positions due to many things such as body part 90 thickness, the make-up of different organs-fluids and various other densities found in the pathway of the x-rays for each position. This means that the examination requires four (4) of the five (5) positions to have a different x-ray exposure settings (providing the x-ray tube is kept at the same fixed distance for each position). The manager may then enter in computer 60 the standard amount of time it should take the operator to perform this examination. In this example the standard amount of time it take to complete this examination will be 20 minutes. The manager also enters in the computer 60 the standard number of the different positions in which body part 90 is placed (and is x-rayed) in order to complete the standard protocol of the examination. In this example it takes five (5) different body part positions to complete the series. This means that a minimum number of five (5) x-ray exposures must be delivered by x-ray tube 10 to body part 90 to produce the five (5) different x-ray pictures of this examination. The manager then enters in computer 60 the name of each of the different positions of body part 90 in the examination as well as the standard order or sequence in which each of the positions are x-rayed. Universally, the first of the five (5) positions normally performed in the examination is called, "the AP or frontal view". In general, AP stands for anterior-posterior and means that the plane or angle of body part 90 faces the x-ray tube 10.

The manager also enters in computer 60 the next or second position generally taken in the examination or series which is called "an Oblique view". There are normally two (2) different oblique views involved in an examination such as of the lumbar spine. An oblique view shows the anatomy that lies in-between the AP or front view and side view of body part 90. This means that to position body part 90 in an oblique view fashion, the operator simply rotates body part 90 by 45 degrees to the right and then by 45 degrees to the left of the AP view. Basically, an oblique view or position requires more radiation (a higher x-ray parameter control dial setting) for the exposure to visualize this particular anatomy of the body part 90 then the amount of radiation then a AP view/position of body part 90. However, both oblique views generally require the same amount of radiation or x-ray parameter control dial setting. Generally speaking, in this particular type of examination one of the oblique views are performed and then the other oblique view is performed immediately after the first oblique position or next in the series.

The manager next enters in computer 60 the fourth position commonly performed in this examination which is called, "the Lateral view". A lateral view is the anatomy of body part 90 that is at a 90 degree angle to the AP or front view of body part 90. That is to say, a lateral view is a side view of body part 90 and may be performed by having the patient continue turning or rotating body part 90 from the last oblique position performed in the examination until the body part 90 is resting completely on its side. In the fifth and final position, the manager enters in computer 60 "the L5-S1 Spot view". The L5-S1 spot view is a detailed magnified picture of the lower or last two vertebrae of this spinal group and the next two vertebrae of the joining vertebral group called, "the sacrum". This view is performed while the patient is still lying on his side.

The manager enters in computer 60, by touching a button that is labeled "protocol completed", to indicate or acknowledge that he has finished creating or building this particular type of standard protocol for this examination.

The following is a brief description of the type of data a manager would enter into computer 60 in order to include a standard protocol program, about a particular type of examination or body part 90, that will produce data which helps monitor the fees and expenses surrounding the examination. The type of data or information that is included in this standard protocol will include: the standard cost to perform the entire examination, the standard cost to perform each position in the examination, the standard amount of time it takes to complete the examination, the standard number of body part positions or views needed to complete the examination, the standard number of exposures needed to complete the examination, the standard wear and tear cost of the x-ray machine to deliver a exposure, the standard film size for each position in the exam, the standard cost for each of the films, the standard cost of the chemicals used to process or develop each size film, the standard cost of the developing machine's wear and tear for each film processed, the standard cost of the x-ray cassettes wear and tear for each exposure, the standard cost for the x-ray room time (so that when time is added to the examination for an extra or repeat picture, this cost whether revenue and/or expense can be added to the examination correctly), the cost or hourly salary of an operator (X-ray Tech) divided into ⅛'s so that every seven and one-half minutes that is added to an examination so can a expense or fee be added for the operators time involved, the standard cost of various medications, the standard cost of various contrast agents, the standard cost of various materials used to perform an examination, etc.

If printer 50 prints out the standard protocol that the manager has created as described above it might read as follows:

| Exam type | Std. # of exposures | Std. # of films | Std. Exam time |
|---|---|---|---|
| Lumbar spine series | 5 | 5 | 20 minutes |

Std. Order of Body Part Positions in Series:
AP, Right/Left Oblique, Lateral and Spot view
Std. Size Film Per Position:
AP=11"×14", Obliques=10"×12", Lateral=11"×14", Spot=8"×10"
Std. Cost Per Film Size:
8"×10"=$3.00, 10"×12"=$4.00, 11"×14"=$5.00, 14"×17"=$6.00
Std Exam Cost:
$280.00
Hourly Salary of X-ray Technologist(Jane Doe):
$40.00

The standard protocol is stored into the computer and remains on the ROM or hard disk ready to be printed out whenever a lumbar spine examination is done. The computer has stored in its memory many different possible examinations such as chest x-ray, hand x-ray, cervical spine x-ray, lumbar spine x-ray, skull x-ray, gall bladder x-ray, kidney x-ray, etc. The computer has stored in its memory dozens if not hundreds of standard protocols bearing numbers. These x-rays are identified by a number. The technologist feeds into the computer a number to bring up the correct protocol for the examination. Computer 60 and/or computer 80 will produce appropriate words to describe the following informalities and others that may occur during the taking of an x-ray:

Hereinafter, I will refer to entries into the computer by the technologist. In this regard, for each body part to be x-rayed, that is for each different type of examination, the computer may be programmed to provide on the computer display a series of prompts that elicit at least some of the information that the technologist enters into the computer. These prompts are omitted from this description in the interest of the brevity.

Having described the standard protocol, I will now describe what is entered by an x-ray technologist who is making actual x-rays of an actual patient, assuming that a physician has directed x-rays of the lumbar spine series. The technologist will then enter into computer 60 all data of the same kind that is included in the standard protocol including any thing that he performs that is not in the standard protocol and omitting any thing that he does not do that is in the standard protocol.

The computer 60 will now compare the standard protocol with the enters made in connection with the actual patient, with the following results.

Assuming that the data entered by the technologist showed that two (2) pictures of the same body position or view were taken one immediately after the other were due to the fact that the patient probably moved during the first picture and therefore the cost of the extra x-ray taken should be charged to the patient. It would therefore add to the standard cost of the examination or fee charged for the services and materials involved in taking the extra picture.

The computer 60 reached the result just decided automatically based on the fact that two (2) identical views were taken in an exam where only one is required one right after the other.

However, a situation where computer 60 would determine that an extra view was the fault of the technologist is as follows.

The technologist enters into computer 60 all data of the same kind that is included in the standard protocol including any thing that he performs that is not in the standard protocol and omitting any thing that he does not do that is in the standard protocol.

The computer 60 will now compare the standard protocol with the enters made in connection with the actual patient, with the following results.

Assuming that the data entered by the technologist showed that two (2) identical pictures or views were taken of body part 90 when only one is required in the exam. However, the second picture was shown to be taken after all of the routine pictures in the series were taken. Also, the second identical picture's exposure setting is different then the first identical pictures setting. That is, the voltage parameter of the second setting is much higher then the voltage parameter of the first picture's exposure setting. Computer 60 found that the second exposure setting shows a better picture of body part 90 and that the first exposure setting showed a poor image quality of body part 90. Computer 60 would therefore not add to the standard cost of the examination the expense or fee for the services and material involved in taking the extra (second) picture. Therefore the cost of the extra x-ray taken should not be charged to the patient, however, computer 60 may add this extra fee to hospital expenses.

The computer 60 may be programmed to reach this result automatically based on the fact that the two (2) identical views were taken not taken right after the other and that the level of the voltage parameter was changed in the second pictures exposure setting.

The computer 60 will now compare the standard protocol with the enters made in connection with the actual patient, with the following results.

The technologist does not enter the input parameters (voltage, Ma and time duration of the exposure) directly to the x-ray tube 10 or to the generator 40 (which is a standard part of the x-ray machine) but enters those parameters in to computer 60 via keyboard 64.

The computer 60 both stores those parameters in its ROM and feeds them to said generator 40, thereby controlling the x-ray machine 10. Alternatively, the said parameter can be entered directly in to generator 40 in which event that would be entered in to computer 60.

The exposure data can be considered a record of what happened, when it happened and/or how it happened. The kind of exposure data created for a particular type of examination is directly related to the kind of data used to create a particular standard protocol for that same examination. In general, each position of body part 90 in a series is different and may require a different amount of radiation than another position in the same series. Each position of body part 90 in a series is taken at a different time frame than another position in the same series. Therefore, the kind of exposure data created about an exposure delivered during a particular examination will normally differ from one exposure to the next in the same examination (such as in the case where an examination might call for several different body positions to be performed such as an AP view, an oblique view, a lateral view,
etc.). Also, the kind of exposure data created about an exposure will differ from one type of patient to another type for the same type of examination such as in the case of an adult chest x-ray examination where a large x-ray film size (14"×17") is needed for the examination vs a small size x-ray film (8"×10") is generally used for an infants chest x-ray examination. Therefore, the size of the film actually used during the x-ray of a actual patient is entered in to computer 60.

The kind of exposure data created about an exposure may also differ from one type of examination to another such as in the case of one type of examination being a routine knee examination which requires three (3) x-ray exposure or x-ray pictures (one AP view and one lateral view) to be taken and the another examination may be a routine hand x-ray exam requiring three (3) exposure or x-ray pictures (one PA view, one oblique view and one lateral view) to be taken. In addition there is a standard protocol program in computer 60 for each type of examination. Operators may review information or data on computer display unit 50. Data may be printed out using printer 70.

After at least one typical standard protocol program has been created about a typical examination, the invention is ready to monitor this same particular exam when an x-ray technologist is ready to use the machine to perform the examination on a patient. The x-ray technologist thru keyboard 64 may input in computer 60 the name of the patient the examination is to be performed on. The x-ray technologist thru keyboard 64 also inputs his/her own identification for the examination. The x-ray technologist may manually input all settings of the apparatus 10 via keyboard 64. The operator selects, using keyboard 64, the type of exam to be performed from a list of exams pre-programmed in computer 60.

The x-ray technologist selects using keyboard 64 which standard protocol computer 60 will create data during the examination. The x-ray technologist next selects the first body position or view in the examination in preparation for the first x-ray. The x-ray technologist then sets via computer 60, the x-ray generator 40 to the correct levels for the exposure. Computer 60 records the date and time of all exposure settings that are made or delivered. The x-ray technologist in the x-ray room, positions the patient or body part 90 for the first x-ray picture in the series or examination. The operator leaves the room to take the x-ray picture. The x-ray technologist presses an exposure or release button for the exposure. This can be done in two ways, first the x-ray technologist pay press a particular key on computer 60, to automatically cause the x-ray tube 10 to release the x-rays 32 and computer 60 automatically records the date and time of the exposure. The second way is for the technologist to directly press the exposure button that controls x-ray tube 10. X-ray tube 10 creates and delivers the first exposure to produce the first x-ray picture in the examination or series.

The x-ray technologist returns to the patient in the x-ray room and position body part 90 for the next position or view (if one is needed) in the examination. The x-ray technologist changes or replaces the x-ray film with a new (undeveloped or unexposed) film. The x-ray technologist leaves the room and selects the name of the next or second position. If necessary, the operator changes, via the computer 60 the parameter setting for this next or second exposure in the examination. The x-ray technologist repeats this process for each of the positions and exposures needed to complete the examination.

When an exposure is delivered, a detector 30 senses that x-rays 32 are made and signals sensor 34 that the exposure is headed toward body part 90. Sensor 34 signals computer 60 that the exposure is being delivered. Computer 60 may record automatically the date and time of day the exposure is delivered as well as the order in the series in which an exposure is delivered during the examination. The x-ray technologist may manually input thru keyboard 64 any necessary exposure data such as the size of film being used for the exposure and any materials need to position body part 90 for the exposure. The operator inputs thru keyboard 64 any necessary data pertaining to the exposure and/or examination that helps identify what happened and what was done to produce an image of body part 90 for a single exposure and/or the entire examination. The operator may press a button to indicate or acknowledge when the examination is completed. After the examination has ended, the operator may select from a menu an option to signal computer 60 to perform certain assumptions or calculations using the exposure data created during the examination and a portion of one of the standard protocols created for this particular type of examination.

When any additional exposure(s), over the standard amount are actually taken by the operator during a particular examination and the examination is completed or has ended, computer 60 and/or computer 80 may analyze the exposure data of that examination and enter (a) the reason why the extra exposure(s) were taken and (b) any pricing data. Computer 60 and/or computer 80 may analyze part or all of the actual exposure data recorded during an examination.

EXAMPLE NO. 1

1. In this first example the technologist will make an examination of the lumbar spine series wherein the patient's movements caused a motion error in one of the pictures. The exposure data recorded for the examination may be as follows:

The technologist enters into keyboard 64 before the examination starts, the name of the patient and the type of examination (lumbar spine) to be performed. The technologist enters into keyboard 64 the time the examination is started. The technologist positions the patient body part 90 for the first view in the series. The technologist enters in computer 60 the name of the first view which is the AP view. The technologist enters in computer 60 a number which identifies the size of the film to be used. Computer 60 will include the cost of the film size based on the standard information in its ROM. The technologist via keyboard 64 sets each parameter to its correct level for the exposure and takes the x-ray. The technologist returns to the room, repositions body part 90 for the next or second exposure in the series. The technologist enters in computer 60 the name of the second view which is the right oblique view in the series. The technologist enters in computer 60 a number for the size of the film to be used. Computer 60 will include the cost of the film size based on the standard information in its ROM.

The technologist operates the computer 60 to set each parameter to the input of the x-ray machine to its correct level for the exposure and takes the x-ray. The technologist returns to the room, repositions body part 90 for the next or third exposure in the series. The technologist enters in computer 60 the name of the third view which is the left oblique view in the series. The technologist enters in the computer a number for the size for the film to be used. Computer 60 will include the cost of the film size based on the standard information in its ROM. The technologist uses the same parameter setting for the left oblique view that was used for the prior right oblique view for the exposure and takes the x-ray. The technologist returns to the room, repositions body part 90 for the next or fourth exposure in the series. The technologist enters in computer 60 the name of the fourth view which is the lateral view. The technologist enters in computer 60 a number for the size for the film to be used. Computer 60 will include the cost of the film size based on the standard information in its ROM. The technologist sets each parameter to its correct level for the exposure and takes the x-ray. The technologist returns to the room and notices that the position of body part 90 is incorrect and decides to repeat (or retake) the view now. The technologist manipulates body part 90 until it is in a satisfactory position for a lateral view again. The technologist enters in computer 60 the name of view this fifth exposure is being delivered for which is the lateral view again. The technologist enters in computer 60 a number for the size for the film to be used again. Computer 60 will include the cost of the film size based on the standard information in its ROM. The technologist operates the computer 60 to use the same parameter setting for this second lateral view as was used for the prior lateral view exposure and takes the x-ray. The technologist returns to the room, repositions body part 90 for the next or sixth exposure in the series. The technologist enters in computer 60 the name of the view for the sixth exposure which is the spot view. The technologist enters in computer 60 a number for the size for the film to be used. Computer 60 will include the cost of the film size based on the standard information in its ROM. Via the computer 60, the technologist sets each parameter of the input to the x-ray machine to its correct level for the exposure and takes the x-ray. The technologist presses a button to signal computer 60 when the examination is completed. The technologist inputs computer 60 with the time the examination ends.

The computer calculates the time duration of the examination and multiplies that duration by the standard dollar amount of the hourly rate of the technologist to obtain the cost in dollars for the services of the technologist. The standard number of exposure and positions to complete the examination of the lumbar spine series in the above example is five (5). Then assume that computer 60 determined from reviewing the exposure data that there were six (6) exposures taken. Further more assume that of the six (6) exposures taken during the exam, two different parameter settings appear twice in this series of exposures. Computer 60 may further find from the exposure data of the examination that the operator selected the lateral view position in the series twice and set the same identical parameter exposure settings both times. Computer 60 may find the exact time when said second identical exposure setting was made during the series. Computer 60 is programmed to conclude (a) that the operator upon returning to the room, after delivering the original lateral position exposure setting may have noticed that the patient's body part 90 was not correctly positioned, and (b) that the operator decided to immediately repeat that same position by slightly manipulating body part 90 into the correct posture now instead of waiting to see if the patient had really moved by checking the developed radiograph later. This is one reason that the second identical setting was made right after or next in the series after the original setting was delivered.

Computer 60 may produce a display (or printed) showing that the amount of time to perform the exam has increased greatly and that the operator's time and the cost of the film is to be charged to the patient. There are many other conclusions that computer 60 may reach, and cause to be displayed, from the exposure data of an examination using the standard protocol data.

A typical exposure data printout of example number 1 would be as follows:

| Patient's name | Exam type |
|---|---|
| John Doe | Lumbar spine series |

Series order of positions:
AP, right/left oblique, lateral, repeat lateral, spot view

| Total # exposures | Total # of extra exposures | Total exam time |
|---|---|---|
| 6 | 1 | 35 minutes |

Exposure # 4. First lateral
view exposure setting: 300 Ma. at 1 Sec. at 80 Kv.p at 40 ins.
Exposure # 5. Second lateral
view exposure setting: 300 Ma. at 1 Sec. at 80 Kv.p at 40 ins.

| Size of extra film | Additional film cost |
|---|---|
| 11" × 14" | $5.00 |
| Additional operator time | Cost of additional time |
| 15 minutes | $10.00 |
| Total additional expenses | Standard examination cost |
| $15.00 | $280.00 |

Add extra expenses of examination to patient's bill   YES X   NO __
Total cost to Patient
$295.00

EXAMPLE NO. 2

2. In this example computer 60 may analyze the exposure data of the examination and conclude that the extra exposure in the series was due to the patient breathing during the exposure which is called "a motion error" in Radiology. The technologist enters into keyboard 64 before the examination starts, the name of the patient and the type of examination (lumbar spine) to be performed. The technologist enters into keyboard 64 the time the examination is started. The technologist positions the patient body part 90 for the first view in the series. The technologist enters in computer 60 the name of the first view which is the AP view. The technologist enters in computer 60 a number for the size for the film to be used. Computer 60 will include the cost of the film size based on the standard information in its ROM. The technologist sets each parameter of the input to the x-ray machines to its correct level for the exposure and takes the x-ray. The technologist returns to the room, repositions body part 90 for the next or second exposure in the series. The technologist enters in computer 60 the name of the second view which is the right oblique view in the series. The technologist enters in computer 60 a number for the size for the film to be used. Computer 60 will include the cost of the film size based on the standard information in its ROM. The technologist sets each parameter of said input to its correct level for the exposure and takes the x-ray. The technologist returns to the room, repositions body part 90 for the next or third exposure in the series. The technologist enters in computer 60 the name of the third view which is the left oblique view in the series. The technologist enters in computer 60 a number for the size for the film to be used. Computer 60 will include the cost of the film size based on the standard information in its ROM. The technologist uses the same parameter setting for the left oblique view that was used for the prior right oblique view for the exposure and takes the x-ray. The technologist returns to the room, repositions body part 90 for the next or fourth exposure in the series. The technologist enters in computer 60 the name of the fourth view which is the lateral view. The technologist enters in computer 60 a number for the size for the film to be used. Computer 60 will include the cost of the film size based on the standard information in its ROM. The technologist sets each parameter to its correct level for the exposure and takes the x-ray. The technologist returns to the room, repositions body part 90 for the next or fifth view and exposure in the series. The technologist enters in computer 60 the name of the view for the fifth view which is the spot view. The technologist enters in computer 60 a number for the size for the film to be used. Computer 60 will include the cost of the film size based on the standard information in its ROM. The technologist sets each parameter to its correct level for the exposure and takes the x-ray. The technologist goes and develops the series of x-rays. The technologist notices on the developed picture that the patient breathed on the lateral or fourth view in the series and must retake this particular view or picture. The technologist returns to the room and repositions body part 90 correctly for the retake of the lateral view. The technologist enters in computer 60 the name of view this sixth exposure is being delivered for which is the lateral view again. The technologist enters in computer 60 a number for the size for the film to be used again. Computer 60 will include the cost of the film size based on the standard information in its ROM. The technologist this time changes two of the parameters levels for the exposure. This change in parameters shortens or reduces the time of the exposure to help eliminate the possibility of the patients breathing habits causing a problem this time. The technologist presses a button to signal the computer when the examination is completed. The technologist may input in computer 60 the time the examination ends. The computer looks that time up in the memory and then multiples the excess time, over the standard amount, by the hourly rate of the technologist. The standard number of exposure (views or positions of the body part 90) to complete the examination of the lumbar spine in the above example is five (5). Computer 60 results may show that the extra (sixth) exposure, added to the examination, was due to involuntary movement of body part 90. Let's say that computer 60 finds that there are two lateral positions labeled in the series. And that although each of the lateral positions have an exposure that will produce similar contrast and detail of the body part 90 being x-rayed one of them has a much shorter exposure time period setting then the other. Computer 60 may further find that the electrical current in milliamperes (MA), flowing to the x-ray tube 10 for the second exposure setting is much larger than the Ma. parameter control dial station for the first (original) setting and that the duration of the time of the exposure for the second setting is reduced substantially compared to the time frame of the first setting. Computer 60 may conclude that the increased or higher Ma. station used for the second exposure setting is done to shorten the time duration for the second exposure setting to eliminate the possibility of demonstrating patient motion during this repeat or retake picture. Computer 60 may further conclude that the motion error was involuntary and that the operator made technical changes to correct the movement problem. Computer 60 may conclude that the added expenses to the examination can not be charged to the patient's bill and that the hospital must absorb this added expense in performing the examination. It is important to know that a technologist may choose to change and/or exchange various parameter levels to eliminate the possibility of a motion error occurring and many other problems. Therefore, computer 60 may review and analyze a parameter being changed in many different ways.

A typical exposure data printout of example number 2 would be as follows:

| Patient's name | Exam type |
|---|---|
| John Doe | Lumbar spine series |

Series order of positions:
AP, right/left oblique, lateral, spot view, repeat lateral

| Total # exposures | Total exam time |
|---|---|
| 6 | 35 minutes |

-continued

First lateral view
exposure setting: 100 Ma. at 1 Sec. at 80 Kv.p at 40 ins.
Second lateral view
exposure setting: 300 Ma. at .30 Sec. at 80 Kv.p at 40 ins.

| Size of extra film | Additional film cost |
|---|---|
| 11" × 14" | $5.00 |
| Additional operator time | Cost of additional operator time |
| 15 minutes | $10.00 |

Hospital Absorbed expenses = $15.00
Total additional cost to patient
$0.00
Add all extra expenses of examination to patient's bill   YES __   NO X
Total cost to Patient
$280.00

EXAMPLE NO. 3

3. In this example computer 60 may analyze the exposure data of the exam and conclude that the extra exposure was due to the fact that the physician in charge of the matter needed an additional view (or picture) of a particular area to help diagnosis the case. The technologist enters into keyboard 64 before the examination starts, the name of the patient and the type of body part 90 (lumbar spine examination) to be performed. The technologist may manually enter via keyboard the start time of the examination or this may be done electronically by computer 60. The technologist positions the patient body part 90 for the first view in the series. The technologist enters in computer 60 the name of the first view which is the AP view. The technologist enters in computer 60 a number for the size for the film to be used. Computer 60 will include the cost of the film size based on the standard information in its ROM. The technologist sets each parameter to its correct level for the exposure and takes the x-ray. The technologist returns to the room, repositions body part 90 for the next or second exposure in the series. The technologist enters in computer 60 the name of the second view which is the right oblique view in the series. The technologist enters in computer 60 a number for the size for the film to be used. Computer 60 will include the cost of the film size based on the standard information in its ROM. The technologist sets each parameter to its correct level for the exposure and takes the x-ray. The technologist returns to the room, repositions body part 90 for the next or third exposure in the series. The technologist enters in computer 60 the name of the third view which is the left oblique view in the series. The technologist enters in computer 60 a number for the size for the film to be used. Computer 60 will include the cost of the film size based on the standard information in its ROM. The technologist uses the same parameter setting for the left oblique view that was used for the prior right oblique view for the exposure and takes the x-ray. The technologist returns to the room, repositions body part 90 for the next or fourth exposure in the series. The technologist enters in computer 60 the name of the fourth view which is the lateral view. The technologist enters in computer 60 a number for the size for the film to be used. Computer 60 will include the cost of the film size based on the standard information in its ROM. The technologist sets each parameter to its correct level for the exposure and takes the x-ray. The technologist returns to the room, repositions body part 90 for the next or fifth view and exposure in the series. The technologist enters in computer 60 the name of the view for the fifth view which is the spot view. The technologist enters in computer 60 a number for the size for the film to be used. Computer 60 will include the cost of the film size based on the standard information in its ROM. The technologist sets each parameter of the input of the x-ray machine 10 to its correct level for the exposure and takes the x-ray. The technologist goes and develops the series of x-ray pictures. The technologist may show the developed pictures to the physician who asked the technologist to take one more x-ray of a particular area at a certain rotation. The technologist returns to the room and repositions body part 90 for the extra or additional view. The technologist enters in computer 60 the name of this sixth view or exposure which is called, "extra view". The technologist enters in computer 60 a number for the size for the film to be used for the extra view. Computer 60 will include the cost of the film size based on the standard information in its ROM. The technologist set the parameters to there correct levels for the exposure and takes the x-ray. The technologist presses a button to signal the computer 60 when the examination is completed. The technologist inputs in computer 60 the time the examination ends. The computer 60 looks that time up in the memory and then multiples the time, over the standard amount, by the hourly rate of the technologist. The standard number of exposure (positions) to complete the examination of the lumbar spine series in the above example is five (5). Computer 60 may conclude that the extra picture and drugs was needed to help further interpret the case and the patient should be billed for all added expenses to the examination.

A typical exposure data printout of the example number 3 would be as follows:

| Patient's name | Exam type |
|---|---|
| John Doe | Lumbar spine series |

Series order of positions:
AP, right/left oblique, lateral, spot view, extra view

| Total # exposures | Total # of extra exposures | Total exam time |
|---|---|---|
| 6 | 1 | 35 minutes |

Exposure # 6.
Added or extra view exposure setting: 250 Ma.S @ 90 Kv.P @ 40 ins.

| Size of extra film | Additional film cost |
|---|---|
| 11" × 14" | $5.00 |
| Additional operator time | Cost of additional time |
| 15 minutes | $10.00 |

Total added expenses to examination
$15.00
Add all extra expenses of examination to patient's bill   YES X   NO __
Total cost to Patient
$295.00

As stated above, computer 60 and computer 80 may be programmed to record an event described under the sections of the Examples numbered 1 to 3 and many more informalities. Also, after computer 60 has recorded its version of the events the operator may enter into the computer 60 his version of the events. This will enable the operator's supervisor and/or the physician to have full information as to how and why any additional x-rays, changes, etc. occurred during an examination.

The review and comparison of the exposure data in the printout may supply Quality Assurance personnel and/or the x-ray technologist with helpful information. The review capabilities of computer 60 may produce the following: How long did an exam take? The order or sequence of each exposure. The exact time each exposure parameter setting is delivered. How long it took the technologist to place the patient in each position and make each exposure. How long it took each operator to perform their examinations daily, weekly etc. How much time is the x-ray machine idle verses the amount of time it is being operated per day, week, year etc. How long the patient was on the table for the exam. Verify the date and time that a particular patient's x-rays were taken. Verify that a particular technologist was using the machine at a specific date and time, etc.

The detector 30 will send a signal to the sensor 34 as long as it intercepts x-rays 32. Since an exposure switch must be depressed by a operator to deliver a dose of radiation, it will be easy to send a signal to computer 60 when the exposure switch is triggered. Many other methods may be used to send a signal to indicate to computer 60 when an exposure is delivered by x-ray tube 10.

Figure 2:
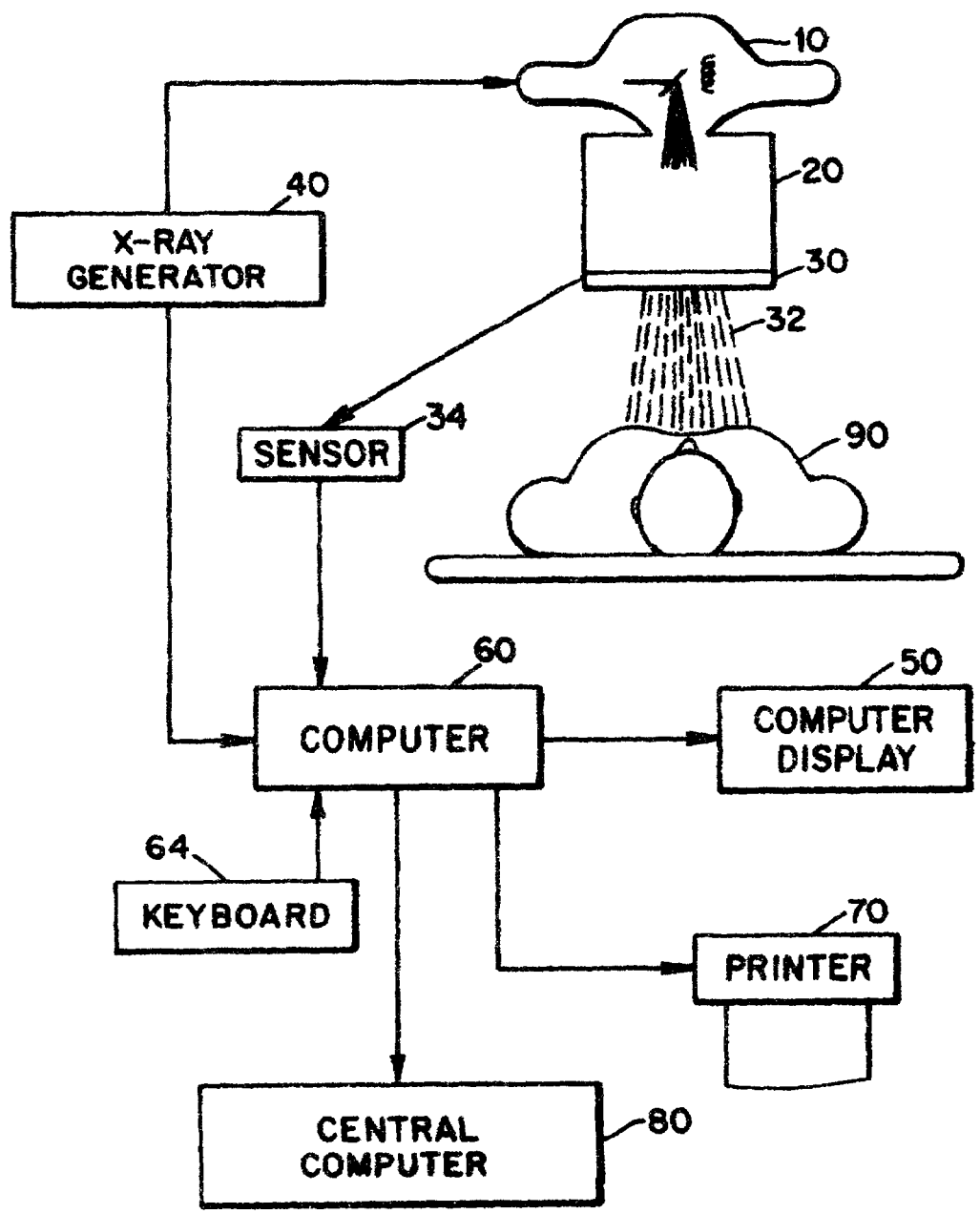
FIG. 2 is a block diagram showing a modified form of the invention.

In the preferred form of the invention as shown in FIG. 1 and FIG. 2 is a mainframe or two (2) computers, computer 60 and computer 80. Some x-ray departments only have one single x-ray machine 10 in the entire department while most other departments have several x-ray machines 10. Computer 80 receives data from computer 60. Digital network system 84 will link all data to the mainframe or computers 60 unit to computer 80 see FIG. 2. Computer 80 may receive some or all of the exposure data as well as standard protocols of computer 60. It must be understood that computer 80 is not attached or connected to any type of imaging machine or x-ray tube 10. Therefore, computer 80 does not and can not monitor x-ray tube 10 or the operator, etc. during the actual performance of an examination. Computer 80 can only receive data from one or more computer 60 unit. Computer 80 is used by a manager (and not an operator) who has more than one x-ray machine 10 in their department, and each of the machines 10 must have a computer 60 unit monitoring it. Computer 80 still has the ability of producing the same results and findings as computer 60 comparing the same data. However, the basic idea behind computer 80 is to process data from more then one computer 60 unit in a department and perform new and different assumptions or calculations on the data from these units. Computer 8 will produce new and different results and/or findings than those normally produced by a single computer 60 unit. Computer 80 receives data from computer 60 and not the other way around. Stored in computer 80 memory are standard protocols like those in the memory of computer 60. Computer 80 also is programmed to produce results that combine the data from each computer 60 that networks data over. Computer 80 combines and compares the data from more then one computer 60 or imaging machine 10 in an entire Radiology department. Computer 80 results give individual as well as combined totals for machines 10, all operators in the department who use any machine 10, all of the patients examined in the department using any machine 10, any particular type of examination or body part 90 performed on any machine 10. Computer 80 produces results and/or findings for example that may show the individual as well as the combined total charges of the day for the entire department, the individual as well as the combined total number of expenses, the individual as well as the combined total number for each type of examination performed, the percentage of the workload a particular operator does, the percentage of the workload a particular machine/room does concerning the entire departments workload, etc.

Therefore, a computer 60 unit can only produce results about the single x-ray machine 10 is connected to and/or the operator who uses this same particular x-ray machine 10. However, computer 80 can not only produce these same results but also produce results about more then one x-ray machines 10 and more then one operators who use the machines 10. The keyboard 64 of computer 80 allows a manager to operate the computer 80. For example, a manager would select via keyboard 64 from a menu a particular type of examination "Lumbar spine" shown on computer display 50 that they want some total results on. Next the manager may select via keyboard 64 the various machines 10 in their department shown on computer display 50 they want to compile these results from. Next, the manager may push a button labeled "calculate total" to perform the computation(s) or add up the total number of Lumbar spines performed on each of the machine 10 they have chosen. Computer 80 will produce an amount, cost, etc. based on the standard information in its ROM. A manager may select via keyboard 64 from a menu the total number of repeat or expenses for any type of exam performed. A manager may select via keyboard 64 the performance record of a specific operator for each type of exam performed, a specific day, etc. Through computer 80 a manager may select via keyboard 64 to combine or compile results about. All results from computer 80 can be shown on computer display 50.

A typical printout of computer 80 would be as follows:
Total # of lumbar spine examinations performed per x-ray machine/room
    Machine/room 1=40 exams
    Machine/room 2=25 exams
    Machine/room 3=0 exams
    Machine/room 4=14 exams
Total # of lumbar spine examinations today=79 exams
Total charges for x-rays=$10,400.00
Total # of a type of examination performed
    # of Chest x-rays=15
    # of Abdomen x-rays=20
    # of Lumbar spine x-rays=22
    # of Hip X-rays=14
    # of Hand/Wrist X-rays=8
Total charges for X-rays=$8,400.00
Total # of extra x-ray retakes performed today=28
Total cost of extra film=$90.00
Total additional operator's time today=280 minutes
Total additional operator's time cost for today=$4,200.00

The above invention has been described in connection with an x-ray machine, however the broader aspects of this invention apply methods for operating other machines that take a picture of the internal anatomy of a body such as MRI scanners, and CT scanners, Ultrasound machines, etc.

I claim:

1. An apparatus for monitoring the operations of an operator of a medical imaging machine that performs a medical function when a patient is positioned for making an image of a body part, and said machine has taken an image of said body part, comprising:
   a computer for storing a first series of steps that an operator should perform when using said medical imaging machine to make said image,
   said computer also storing a second series of steps that the operator took when he or she used the machine to make an image of a body part of a human being,
   said computer comparing said first series of steps with said second series of steps; and
   said computer having an output based on the information developed from the differences between said first series of steps and said second series of steps.

2. Apparatus as defined in claim 1, in which said computer has an output which sets forth prices computed from the operations performed by the operator of said medical imaging machine.

3. Apparatus as defined in claim 1, in which there are plural medical imaging machines and plural computers, including at least one computer for each medical imaging machine so that separate operators of said medical imaging machines can be monitored for separate patients at the same time.

4. The apparatus as defined in claim 1, in which said first series of steps includes the manipulations an operator should perform in performing said medical function, said second series of steps including the manipulations performed by said operator in using said medical imaging machine.

5. The apparatus as defined in claim 1, in which said first series of steps includes the manipulations of the patient which should be performed during said medical procedure, said second series of steps including actual manipulations of the patient during said medical procedure.

6. The apparatus as defined in claim 1, in which said computer stores a signal that represents the operations of the operator.

7. The apparatus as defined in claim 1, in which said computer compares the cost of performing said first series of steps with said second series of steps.

8. The method of monitoring the operations of a human operator of a medical imaging machine in the taking of one or more pictures of a body part of a male or female patient, comprising:

providing a computer having a memory, providing the computer with facilities for inputting information, providing the computer with facilities for outputting data, positioning of the body part of said male or female patient in the desired location for taking said picture, storing in said computer information representing at least two predetermined steps that said human operator should perform when using said medical imaging machine to take a picture of a body part of said male or said female patient, storing in said computer information representing at least two of the actual steps that said human operator did perform when using said medical imaging machine to take a picture of a body part of said male or said female patient, comparing, by the computer, said at least two predetermined steps with said at least two actual steps that were entered into said computer, and providing an output from said computer that was at least partially derived from said comparison.

9. The method as defined in claim 8, in which said computer computes prices useful, for billing purposes, from the operations of said medical imaging machine.

10. The method as defined in claim 8, in which there are a plurality of medical imaging machines each of which perform a medical function, providing a separate operator for each of said medical imaging machines, with each operator performing a series of steps while operating a machine, and comparing said predetermined series of steps with the actual series of steps of each operator.

11. The method as defined in claim 10, in which said computer provides information on procedures performed on each of said medical imaging machines as well as summaries of the operations of all of said medical imaging machines.

12. The method as defined in claim 8, in which said first named series of steps includes the manipulation the operator should perform in using the medical imaging machine.

13. The method as defined in claim 8, in which said computer stores as part of said predetermined series of steps the operator's manipulation of the patient which should be performed as part of said medical function, said actual series of step including the operator's actual manipulations of the patient, said computer also computing at least some part of the cost of some part of the medical procedure performed.

14. The method as defined in claim 8, in which said computer has more than one stored signal which represents the operations of the operator during the performance of the medical procedure.

15. The method as defined in claim 8, in which said computer prints out the results of said computer comparison of said predetermined series of steps with said actual series of steps along with pricing data relating to said operation.

16. The method as defined in claim 8, in which said computer stores the physical steps that took place in performing a procedure, and determines data useful in computing the cost of operating said machine.

17. An apparatus for monitoring the operations of an operator of a medical imaging machine to take a picture of a body part of a patient, comprising:

a computer, said computer including means for storing at least two predetermined steps that an operator should perform when using said medical imaging machine to take a picture of a body part of a patient, said computer including means for receiving and storing at least two of the actual steps that the operator did perform when using said medical imaging machine to take a picture of a body part of a patient, and said computer also including means for comparing said at least two predetermined steps with said at least two actual steps entered into said computer and for outputting a result of said comparison.

18. The apparatus as defined in claim 17, in which said computer stores signals representing the operator's operations during the medical procedure.

\* \* \* \* \*